United States Patent [19]

Polk, Jr. et al.

[11] Patent Number: 5,282,978
[45] Date of Patent: Feb. 1, 1994

[54] SPECIMEN PROCESSOR METHOD AND APPARATUS

[75] Inventors: Lewis T. Polk, Jr., Bedford, Mass.; Todd E. Bottomley, Spofford, N.H.; Phillip P. Brown, Westford, Mass.

[73] Assignee: Cytyc Corporation, Marlborough, Mass.

[21] Appl. No.: 948,133

[22] Filed: Sep. 21, 1992

Related U.S. Application Data

[63] Continuation-in-part of Ser. No. 937,247, Aug. 28, 1992, which is a continuation of Ser. No. 550,142, Jul. 9, 1990, Pat. No. 5,143,627.

[51] Int. Cl.$^5$ .............................................. B01D 37/00
[52] U.S. Cl. ..................... 210/767; 210/142; 210/232; 210/252; 210/295; 422/63; 422/99; 422/101
[58] Field of Search ................. 210/767, 739, 142, 97, 210/143, 232, 241, 252, 295; 422/58, 62, 63, 101, 99; 436/177, 180

[56] References Cited

U.S. PATENT DOCUMENTS

| | | |
|---|---|---|
| 3,647,632 | 3/1972 | Johnson et al. |
| 3,900,290 | 8/1975 | Honstra .................. 422/73 |
| 4,166,768 | 9/1979 | Tolbert et al. ............ 435/286 |
| 4,391,710 | 7/1983 | Gordon ................... 210/361 |
| 4,395,493 | 7/1983 | Zahniser et al. .......... 435/289 |
| 4,435,507 | 3/1984 | Stenkvist ................ 435/262 |
| 4,468,410 | 8/1984 | Zeya ..................... 427/2 |
| 4,583,396 | 4/1986 | Hunt et al. ............. 73/61.73 |
| 4,647,376 | 3/1987 | Galaj .................... 210/297 |
| 4,670,147 | 6/1987 | Schoendorfer ............ 210/541 |
| 4,755,300 | 7/1988 | Fishel et al. ............ 210/650 |
| 4,790,942 | 12/1988 | Shmidt et al. ........... 210/650 |
| 5,019,512 | 5/1991 | Varecka et al. .......... 435/240.25 |
| 5,143,627 | 9/1992 | Lapidus et al. .......... 210/232 |

FOREIGN PATENT DOCUMENTS

| | | |
|---|---|---|
| 1178183 | 11/1984 | Canada . |
| 0224962 | 6/1987 | European Pat. Off. . |
| 0244999 | 11/1987 | European Pat. Off. . |
| 0368621 | 5/1990 | European Pat. Off. . |
| 3338782 | 5/1985 | Fed. Rep. of Germany . |
| 63-202372 | 8/1988 | Japan . |
| WO89/09279 | 10/1898 | PCT Int'l Appl. . |

Primary Examiner—Robert A. Dawson
Assistant Examiner—Sun Uk Kim
Attorney, Agent, or Firm—Lahive & Cockfield

[57] ABSTRACT

A specimen processor, for operation with holder apparatus carrying a viewing screen and a filter device and a container of a biological sample, has a frame with reference structure for aligningly engaging the holder apparatus, and has a transport that carries a manipulation device. The processor operates the transport and the manipulation device to engage the filter device, remove it from support by the holder apparatus and collect cellular particles from the sample onto the filter device. The processor further operates the transport and manipulation device to abut the filter device with the viewing screen for transferring collected cellular particles to the screen, and to return the filter device to carrying by the holder apparatus.

16 Claims, 16 Drawing Sheets

SPECIMEN PROCESSOR METHOD AND APPARATUS

CROSS REFERENCE

This application is related to the commonly assigned and concurrently filed application for patent Ser. No. 948,304 entitled "Clinical Cartridge Apparatus", and is a continuation-in-part of the co-pending and commonly assigned U.S. application for patent Ser. No. 937,247, filed on Aug. 28, 1992, entitled "Method And Apparatus For Preparing Cells For Examination", which is a continuation of U.S. application for patent Ser. No. 550,142, filed on Jul. 9, 1990, now U.S. Pat. No. 5,143,627, issued Sep. 1, 1992.

BACKGROUND

This invention generally relates to the field of particle collection and transfer. The invention provides a method and apparatus for collecting a quantity of particles from a liquid, such as cells from a biological sample, and transferring the particles onto a glass slide or other viewing screen. The invention is useful in cytology, which is a medical and laboratory science that makes diagnoses based on examination of cells.

More particularly, this invention relates to specimen processor that operates with a cartridge-like transport or holder. The processor operates with the holder to collect a quantified clinical specimen from sample material carried with the holder, and to transfer the specimen to a viewing screen, also carried with the holder.

The specimen processor apparatus and method of the invention are advantageously used, in at least one instance, in the clinical laboratory processing of a biological sample. More particularly, they are used in clinical laboratory processing in which cellular particles are collected from a liquid suspension of the sample and transferred to a microscope slide for examination, either electro-optically or by human viewing. The cellular particles are, as is advantageous, applied to the slide with essentially a monolayer and uniform distribution.

The term "cellular particle" is used herein to encompass cells, cell fragments and clusters or groupings of cells and/or cell fragments.

Clinical laboratory diagnostic testing with a monolayer distribution of cellular particles on a microscope slide, and apparatus and methods for performing such testing of the type with which the invention is advantageously practiced, are described in U.S. Pat. No. 5,143,627; in co-pending U.S. application for patent Ser. No. 843,571; and in the commonly assigned and concurrently filed application entitled "Clinical Cartridge Apparatus". The disclosures of these documents are incorporated herein by this reference.

The U.S. Pat. No. 5,143,627 describes an instrument for collecting a quantitatively measured number of biological cellular particles from suspension in a liquid sample and for transferring the counted collected particles, with an essentially monolayer and uniform distribution, to a viewing screen, typically a microscope slide. The instrument has disposable elements and containers that contact the sample material and accordingly that require replacement between the processing of successive samples, to avoid inter-sample contamination.

OBJECTS

It is accordingly an object of this invention to provide specimen processing methods and apparatus, for use in the preparation of a spatially distributed cellular specimen on a microscope slide or other viewing screen, with minimal concern for inter-sample contamination. A more specific object is to provide a sample processing method and apparatus capable of automated operation with multiple samples in sequence, with minimal operator intervention between samples, and yet with relatively high reliability, repeatability, accuracy, and precision, as well as minimal inter-sample contamination.

Another object of the invention is to provide such automated apparatus, for preparing cellular particles for examination, that attains high inter-sample isolation with self-containment of waste material.

Other objects of the invention will in part be obvious and will in part appear hereinafter.

SUMMARY OF THE INVENTION

A clinical system according to this invention resolves problems associated with known equipment for collecting particles, such as cells for cytology. The system provides a mechanism of relatively simple structure and operation which disperses particles, such as cells, in a liquid solution, collects an approximately known quantity of the particles from the solution, and presents the collected quantized particles, with a single layer spatial distribution, for transfer to a viewing screen. The system can also transfer the particles, with the same spatial distribution, to the viewing screen. Another feature is that the system attains a particle distribution which is substantially uniform, and, further, which has a substantially uniform number of cells per unit area.

The clinical system has two main components, a cartridge and a specimen processor. The cartridge includes a mechanism for removably and replaceably supporting a fluid-confining vessel having a filter element. The filter element may be of the screen, membrane, or other type which is suitable for passing liquid and particles below a threshold size and for blocking and hence collecting, on a surface, target particles above the threshold size.

Another element of the cartridge is a mechanism for removably and replaceably supporting a microscope slide or other viewing screen. The cartridge can dispose the slide for receiving particles collected on the filter element. The cartridge further includes structure for supporting a container of particle-suspending sample solution. The cartridge preferably also includes structure for supporting a slide preparation output container, typically containing a fixative solution.

A further element of the cartridge is a mechanism that can be actuated to transfer a microscope slide to the output container.

The specimen processor has a reference structure for alignment with the cartridge. When so aligned, the cartridge is arranged for interacting with the processor, which includes structure for introducing the filter element of the fluid-confining vessel into the particle-suspending sample liquid, as well as structure for producing shear forces in the liquid for dispersing cellular particles.

After the processor introduces the filter element into the particle-suspending sample liquid and disperses particles, a pneumatic unit of the processor, which the processor removably couples to the fluid-confining vessel, draws sample liquid into the vessel for collecting particles on the filter surface. Particles of interest collect on the filter surface and block fluid flow through the filter element. Accordingly, since there is no fluid flow through the filter element in the area where particles have collected, the particles collect in a single layer against the filter. The resultant spatial distribution of the particles collected on the filter element facilitates effective examination of the particles once they are transferred to a viewing screen. Sensor elements of the pneumatic unit, together with a control unit of the specimen processor, monitor this cell-collecting operation by monitoring parameters of the liquid flow to determine when a selected quantity of dispersed particles is collected on the filter element.

In some embodiments of the invention, the cartridge includes structure for supporting a viewing screen and for supporting an output container. In these embodiments, the specimen processor includes structure for disposing the filter element in an essentially face to face relationship with the viewing screen and for transferring the collected target particles from the filter element to the viewing screen, while maintaining the selected spatial distribution of the particles attained during collection.

Also in these embodiments of the invention, the specimen processor includes an actuating mechanism for actuating a transfer mechanism on the cartridge to release the viewing screen with transferred target particles thereon. The transfer mechanism guides or otherwise transfers the viewing screen into the output container, which typically contains a fixative solution. In this manner, the transferred particles are prepared for further processing.

Apparatus according to the invention thus enables a machine, termed a specimen processor, to process a biological sample to prepare a cytologic or other clinical specimen for examination, and isolates sources of inter-sample contamination from the specimen processor. The invention thus enables the specimen processor to process successive samples without cleaning and without risk of inter-sample contamination.

The cartridge-like holder or carrier apparatus that invention provides operates with the mechanized processor for collecting cellular particles from a fluid sample and for transferring the particles with a selected distribution to a microscope slide or like viewing screen. The cartridge carries the sample material and all implements that come in contact with the sample. It is arranged so that the mechanized processor is not contaminated by the sample material.

A separate, fresh cartridge according to the invention is employed for each biological sample. Each cartridge brings to the mechanized processor the sample and all disposable devices, i.e., sample contacting implements. Further, the cartridge receives the final prepared specimen and all waste materials and disposables. The mechanized processor, as a result, remains clean of contact with the sample and can operate with successive samples, by way of separate cartridges, without inter-sample cleaning and without risk of inter-sample contamination.

The invention accordingly comprises the features of construction, combinations of elements and arrangements of parts exemplified in the constructions hereinafter set forth, all as exemplified in the following detailed disclosure, and the scope of the invention as indicated in the claims.

BRIEF DESCRIPTION OF THE DRAWING

For a fuller understanding of the nature and objects of the invention, reference is to be made to the following detailed description and the accompanying drawings, in which.

DESCRIPTION OF ILLUSTRATED EMBODIMENTS

Figure 1:
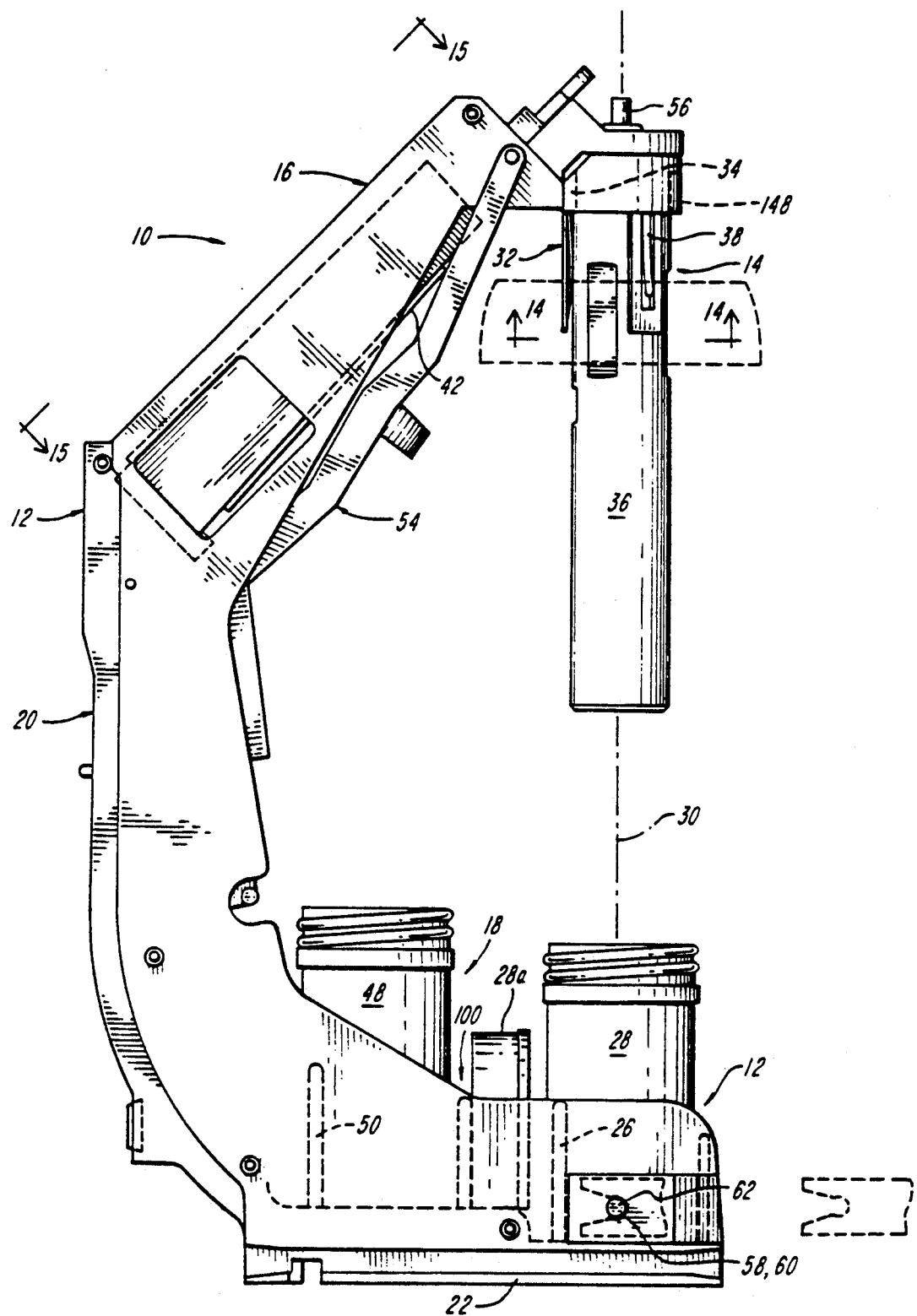
FIG. 1 is a side elevation view of a cartridge according to the invention carrying a sample container, an output container, a microscope slide, and a filter device.
Figure 2:
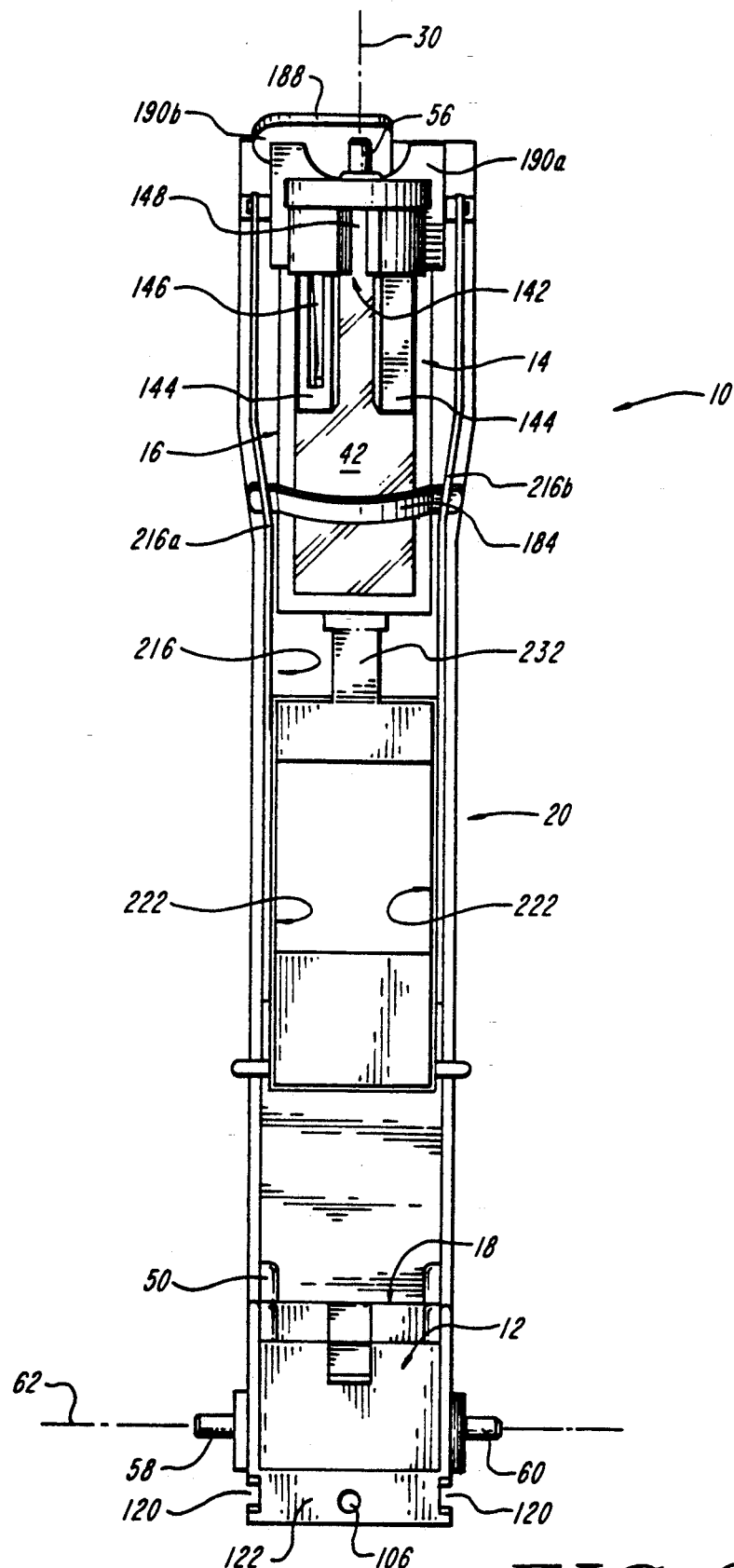
FIG. 2 is a front elevation view of the cartridge of FIG. 1.

FIGS. 1 and 2 show a cartridge 10 according to the invention for operation with a specimen processor according to the invention, as discussed below with references to FIGS. 4–10. The cartridge 10 has an upright frame 20 with a base 22, and has four supports 12, 14, 16, and 18, each of which removably and replaceably receives and holds a clinical implement.

A first of the four supports is a sample support 12, lowermost on the illustrated cartridge 10, and formed with upright sample guides 26. The sample guides 26 and base 22 form the sample support 12 as essentially a socket-like receptacle that telescopically receives a sample container 28 oriented upright and centered on a normally vertical axis 30.

A second support on the cartridge 10 is a first implement support 14 located uppermost on the cartridge, adjacent the top of the frame 20. The first implement support 14 includes a downwardly facing tubular socket-like receptacle 32 centered on the axis 30. The support 14 includes a rotational guide, illustratively formed with an axial slot 34 recessing the wall of the receptacle 32, for imparting a selected rotational orientation, relative to the vertical axis 30, of a filter device 36 seated therein. The illustrated implement support 14 also has a leaf spring 38 arranged for resiliently engaging a filter device 36 seated in the support for removably and replaceably holding the filter device in the support.

A third support on the cartridge is a second implement support 16 for holding a microscope slide 42. The illustrated support 16 has a breach-like mechanism into which a slide 42 is loaded and then clamped. The support positions the clamped slide to receive a distribution of cellular particles collected from a sample in the sample container 28.

The illustrated fourth support is an output support 18 that can be structured similar to the sample container support 12 to receive an output container 48 at a selected lower location on the cartridge 10. The illustrated output support 18 accordingly employs upright container guides 50 that, together with the base 22, provide a socket-like receptacle for receiving and locating an upright output container 48.

A further feature of the illustrated cartridge 10 is a transfer mechanism 54 on the frame 20 that, as described further below and shown in FIG. 11, removes a microscope slide 42 from the support 16 and transfers it to an output container 48 at the output support 18. The illustrated transfer mechanism 54 guides the gravitational descent of a microscope slide 42 that has been released from the second support 16, for transferring the slide into an output container 48 seated in the output support 18.

The illustrated cartridge 10 has three triangularly located reference structures, illustrated as cylindrical reference pins 56, 58, and 60, for removable and replaceable engagement with mating reference structures of a specimen processor. Two reference pins 58 and 60 project in opposite directions from the frame 20 along a normally horizontal axis 62 transverse to the vertical axis 30. The third reference pin 56 projects from the top of the cartridge frame 20 and is axially centered and aligned with the vertical axis 30.

The supports 12 and 14 and the reference pin 56 of the illustrated cartridge 10 are aligned and centered on the normally vertical axis 30. Accordingly, the sample container 28 seated in the support 12 and the filter device 36 seated in the support 14 are likewise aligned and centered on the axis 30. Further, the illustrated four supports are aligned along and centered on a plane through the axis 30 and parallel to the plane of FIG. 1. the concurrently-filed and commonly assigned application for patent entitled "Clinical Cartridge Apparatus" discloses further structure and operation of the cartridge 10.

Figure 3:
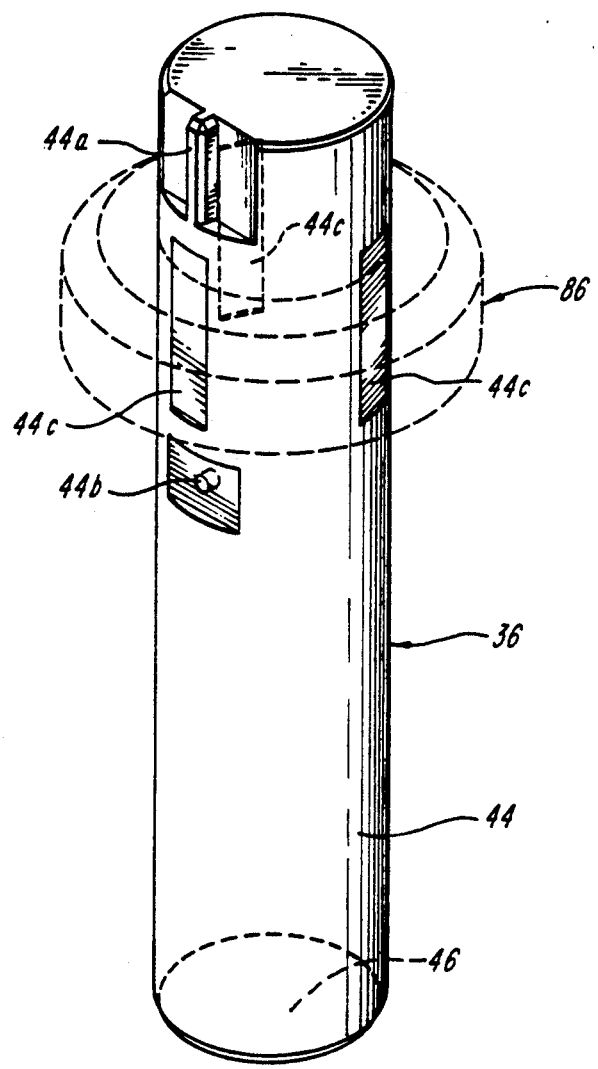
FIG. 3 is a perspective view of a filter device for use with the cartridge of FIGS. 1 and 2.

The illustrated filter device 36, shown in FIG. 3, has a hollow cylindrical body 44 closed at a normally upper axial end and having a screen filter 46 spanning across a normally lower axial end. The screen filter has pores of selected size to block cells and cellular particles of interest and to pass smaller particles. An orienting tab 44a projects radially from a flattened surface portion of the body, adjacent the closed end. The tab 44a is preferably within, and hence does not project beyond, the cylindrical outer surface of the body 44. A passage 44b extends radially through the wall of the body 44 at a location axially aligned with the tab 44a and well space from both axial ends to be in the middle portion of the body. The cylindrical outer surface of the body is flattened at the passage 44b, so that the passage extends from the center of the flattened recess in the body outer wall.

A further structure feature of the illustrated filter device 36 is a clamping region located axially between the aligning tab 44a and the passage 44b, and having a non-circular cross-section. The illustrated non-circular clamping region is formed by three flat clamping surfaces 44c uniformly spaced about the circumference of the cylindrical body 44. This set of clamping surfaces has a selected or known circumferential location and axial location on the device 36, relative to the tab 44a and the passage 44b. Co-pending and commonly-assigned U.S. application for patent Ser. No. 07/843,571 discloses the structure and manufacture of filter devices similar to the filter device 36, and such similar filter devices are marketed by Cytyc Corporation of Marlborough, Mass., U.S.A.

Figure 4:
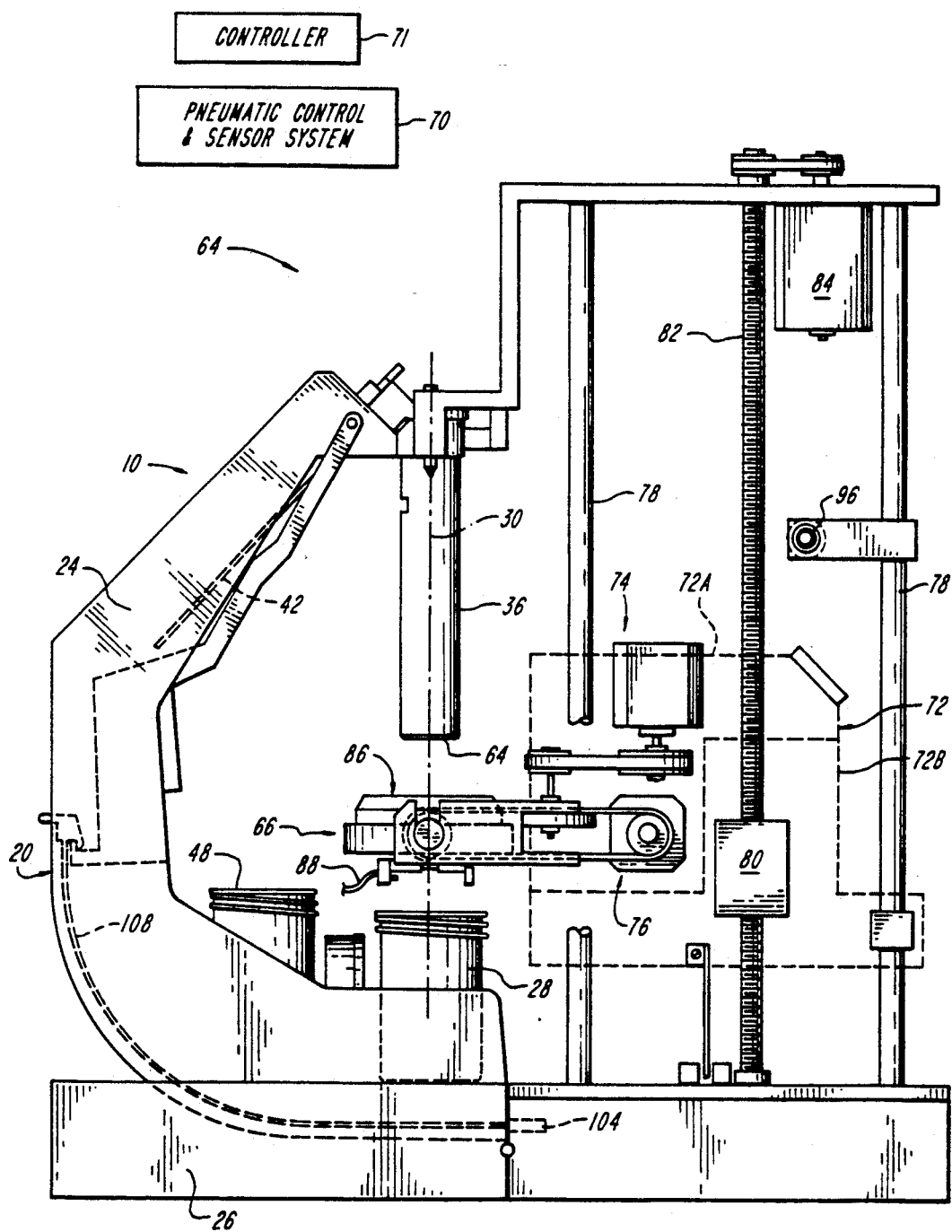
FIGS. 4 through 10 are side elevation views, partly simplified and partly diagrammatic, of the cartridge of FIGS. 1 and 2 operatively engaged with a specimen processor and showing different stages of the processor operation with the cartridge according to the invention.

FIG. 4 shows the cartridge 10 of FIGS. 1 and 2 engaged with a specimen processor 64 that has a manipulator 66 coupled with a multi-axial drive system and coupled with a pneumatic control system 70. During operation of the specimen processor 64 with a cartridge 10, the manipulator 66 is aligned initially with the vertical axis 30 of the cartridge 10 as appears in FIG. 4 and disposed vertically above the sample container 28 and below the filter device 36 that the cartridge carries.

The illustrated processor 64 has an extendable two-part carriage 72 that mounts the manipulator 66 on a carriage platform 72a. The carriage platform 72a carries a rotational drive mechanism 74 coupled with the manipulator and carries a tilt drive mechanism 76 also coupled with the manipulator 66. A second carriage platform 72b carries the platform 72a and is slideably mounted on two parallel elevator slide rods 78. The second platform is coupled by way of a nut block 80 with a lead screw 82 driven by an elevator motor 84.

The specimen processor 64 operates with a controller 71, typically employing a micro processor, and with the pneumatic control and sensing system 70. EPO Publication No. 0448837A3 describes one preferred construction for the pneumatic system 70.

In the illustrated system of FIG. 4, the cartridge 10 operates with the specimen processor 64 through a sequence of stages for collecting a biological specimen from the sample in the cartridge-carried container 28 and for transferring it to a microscope slide 42 carried on the support 16 of the cartridge.

Figure 5:
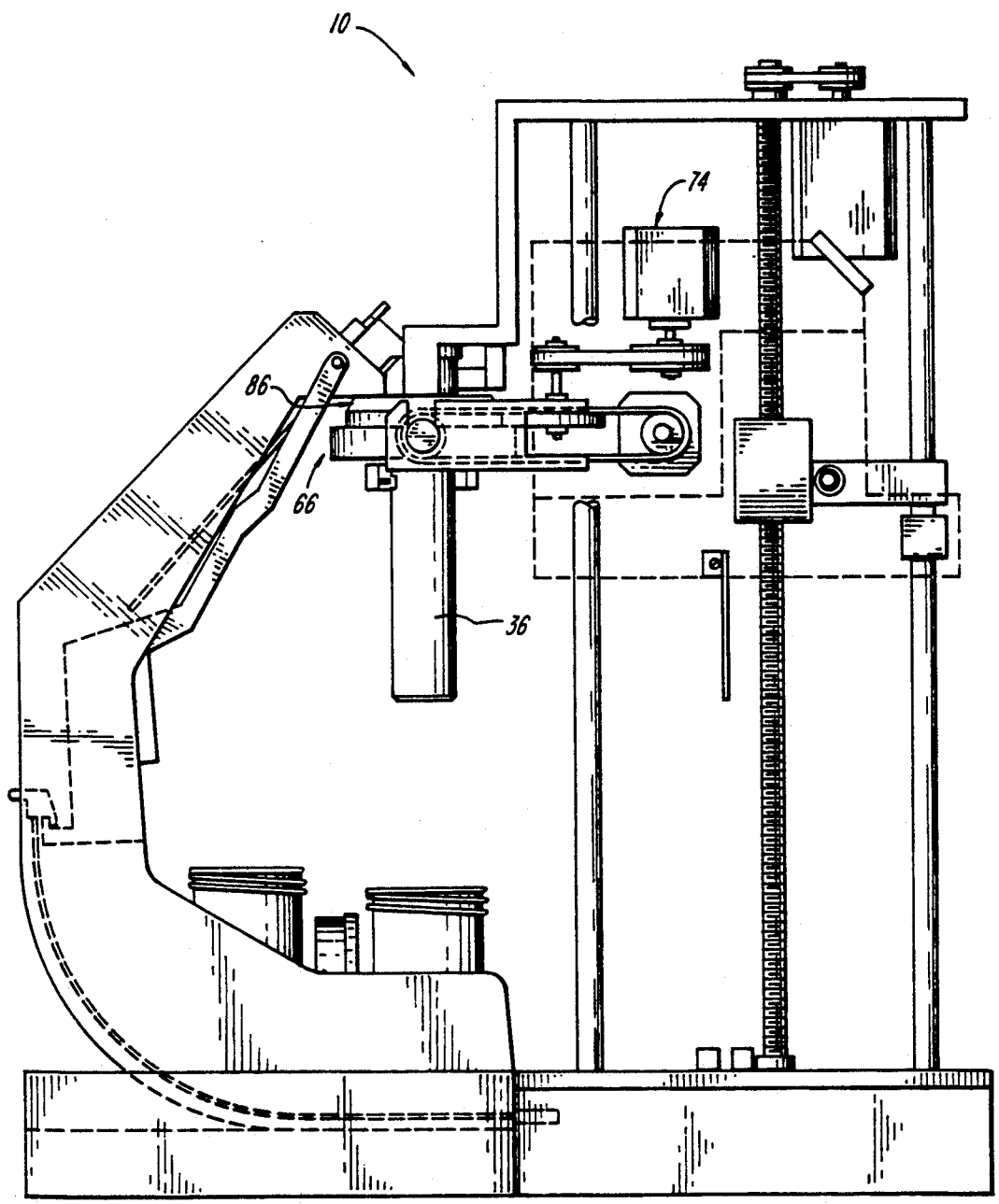

In a first operating stage, subsequent to the initial engagement stage in which the cartridge 10 is operatively engaged with the processor 64 as shown in FIG. 4, the elevator motor 84 rotates the lead screw 82 to raise the carriage 72 to an uppermost position shown in FIG. 5. This upward movement raises the manipulator 66 to slide upward relative to the filter device 36 mounted on the cartridge 10. The illustrated manipulator 66 has a circular jaw mechanism 86 centered on the axis 30 in the initial condition of FIG. 4 and that is initially in an unclamping condition where it telescopically fits over the body 44 of the filter device 36. The upward elevational movement of the carriage thus positions the manipulator 66 in the clamp position shown in FIG. 5, where the jaw mechanism 86 essentially encircles the filter device at the clamping surfaces 44c. The jaw mechanism has two jaw elements that can be locked to rotate together and that can be unlocked to rotate relative ton one another. This relative rotation moves radial clamping jaws into and out of clamping engagement with the body of the filter device 36.

With the processor 64 in the clamp position of FIG. 5, the rotational drive mechanism 74 operates the circular jaw mechanism 86 of the manipulator 66 to clamp the jaw mechanism onto the tubular body 44 of the filter device 36. The illustrated drive mechanism 74 performs this clamping operation by rotating one of two jaw elements of the jaw mechanism 86 about the vertical axis 30 relative to the other jaw element to affect a radially inward clamping action onto the three clamping surfaces 44c on the body of the filter device 36.

After clamping the manipulator 66 onto the filter device 36, the processor 64 rotates the lead screw 82 to lower the carriage 72 and thereby lower the manipulator 66. This downward movement of the manipulator 66 lowers the filter device 36, which is clamped to the manipulator, thereby removing the filter device 36 from the implement support 14 of the cartridge 10 and eventually immersing the lower end of the filter device into the biological sample contained in the sample container 28, as FIG. 6 shows.

Figure 6:
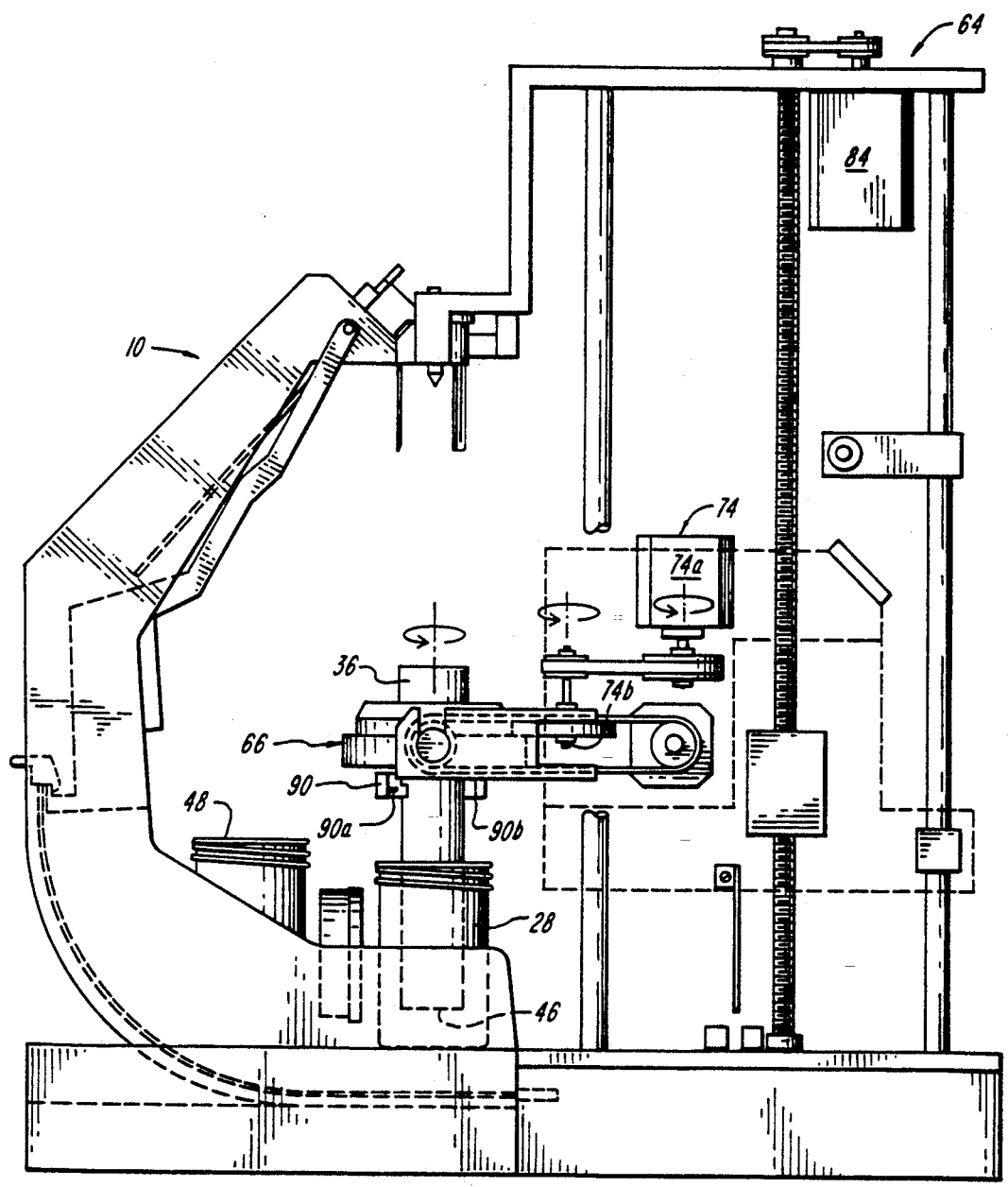

One operation of the specimen processor 64 when in the disperse position of FIG. 6 is to spin the filter device 36 about the vertical axis 30 to subject the biological sample in the container 28 to shear forces that disaggregate particles in the liquid sample solution. The illustrated processor 64, to this end, actuates the rotational drive mechanism 74 to spin the clamped filter device 36. In particular, the illustrated rotational drive mechanism 74 operates a motor 74a coupled by a belt and pulley with a shaft that carries a drive wheel 74b, the rim of which is engaged to rotate the jaw mechanism 86. FIG. 6 designates with the three arrows the rotation of the motor 74a, the rotation of the drive wheel 74b and the resultant rotation of the manipulator jaw mechanism 86 and the filter cylinder 36 clamped therein.

After this particle dispersing action, the processor controller 71 stops the drive mechanism 74 and actuates the pneumatic control system 70 for collecting a specimen of cellular particles from the sample in the container 28 onto the screen filter 46 of the filter device 36. The above-noted EPO Patent Publication No. 0448837A3 and U.S. Pat. No. 5,143,627 describe a preferred specimen collecting operation. For this operation, the pneumatic control system 70 applies a selected negative pressure preferably a series of negative pressure pulses separated by pressure-sensing intervals to the interior of the filter device 36 by way of a pneumatic hose 88 connected between the pneumatic system 70 and a pneumatic coupling clamp 90 on the manipulator 66.

Figure 7:
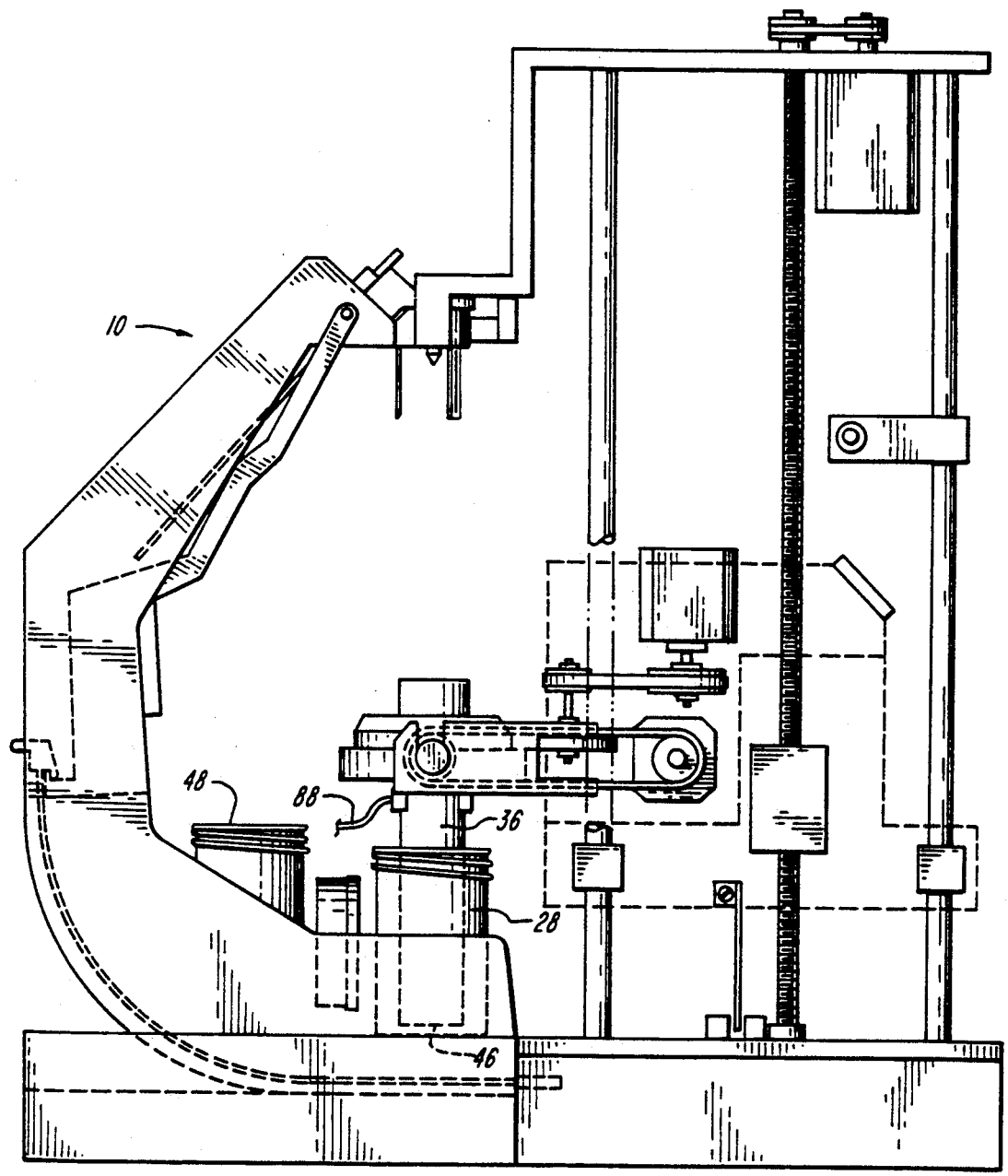

The illustrated pneumatic coupling clamp is a solenoid-actuated caliper, having caliper arms 90a and 90b disposed on opposite sides of the clamped filter device. The clamp 90 is open, with the clamp arms spaced away from the filter cylinder 36, when the processor 64 is in the positions of FIGS. 4, 5, and 6. FIG. 7 shows the clamp in the closed condition, where the arms 90a and 90b are clamped against the body 44 of the filter device. The clamp arm 90a carries a pneumatic coupling, connected to an end of the hose 88, which connects to the filter device passage 44b (FIG. 3) when the clamp 90 is closed.

In one preferred embodiment, the hose 88 has two separate passages and the clamp arm 90a forms a wye-like fitting that connects both hose passages in parallel to the filter device passage 44b. The pneumatic system 70 couples one passage of hose 88 to a pressure source and connects the other hose passage to a pressure sensor, for sensing pressure inside the chamber of the filter device 36.

Accordingly, when the clamp 90 is closed, FIG. 7, the pneumatic system 70 can apply a selected positive pressure signal, and conversely a selected negative pressure signal, to the interior chamber of the filter device. The pneumatic system applies a negative pressure signal to the filter device 36 to draw sample liquid into the device from the sample container 28, and thereby deposit cellular particles of the sample onto the filter screen of the filter device 36. After a selected quantity of cellular particles are collected on the screen filter of the filter device 36, as determined by sensing pressure in the interior chamber of the filter device, by way of the passage 44b and the hose 88, with the pneumatic system 70 operating in conjunction with the controller 71, the pneumatic signal terminates.

The processor 64 preferably performs a further operation, with the pneumatic system 70 and the clamp 90, during the transition from the FIG. 5 operation of clamping the filter device 36 and the dispersing operation of FIG. 6. This further operation can sense the level of liquid in the sample container 28. Steps of this further operation are to close the clamp 90 and apply a negative pressure to the chamber of the filter device as the carriage 72 descends from the raised position of FIG. 5 to the lowered position of FIG. 6, and thereby as the filter screen 46 on the clamped filter device is lowered into the sample container liquid. The pneumatic system 70 can sense the transition when the screen filter 46 first enters the sample liquid. The pneumatic system 70 preferably applies a negative pressure signal having a series of negative pressure pulses separated by pressure-sensing intervals. The above-noted EPO publication discloses the operation of a pneumatic system with such a pulsed pressure signal.

The specimen processor 64 proceeds from the collection position of FIG. 7 to a transfer position with several steps. A first step is to raise the filter device 36 clamped in the manipulator 66, with the collected specimen of cellular particles on the screen filter 46, by operating the elevator motor 84 to raise the filter device sufficiently to withdraw it from the sample container 28.

Figure 8:
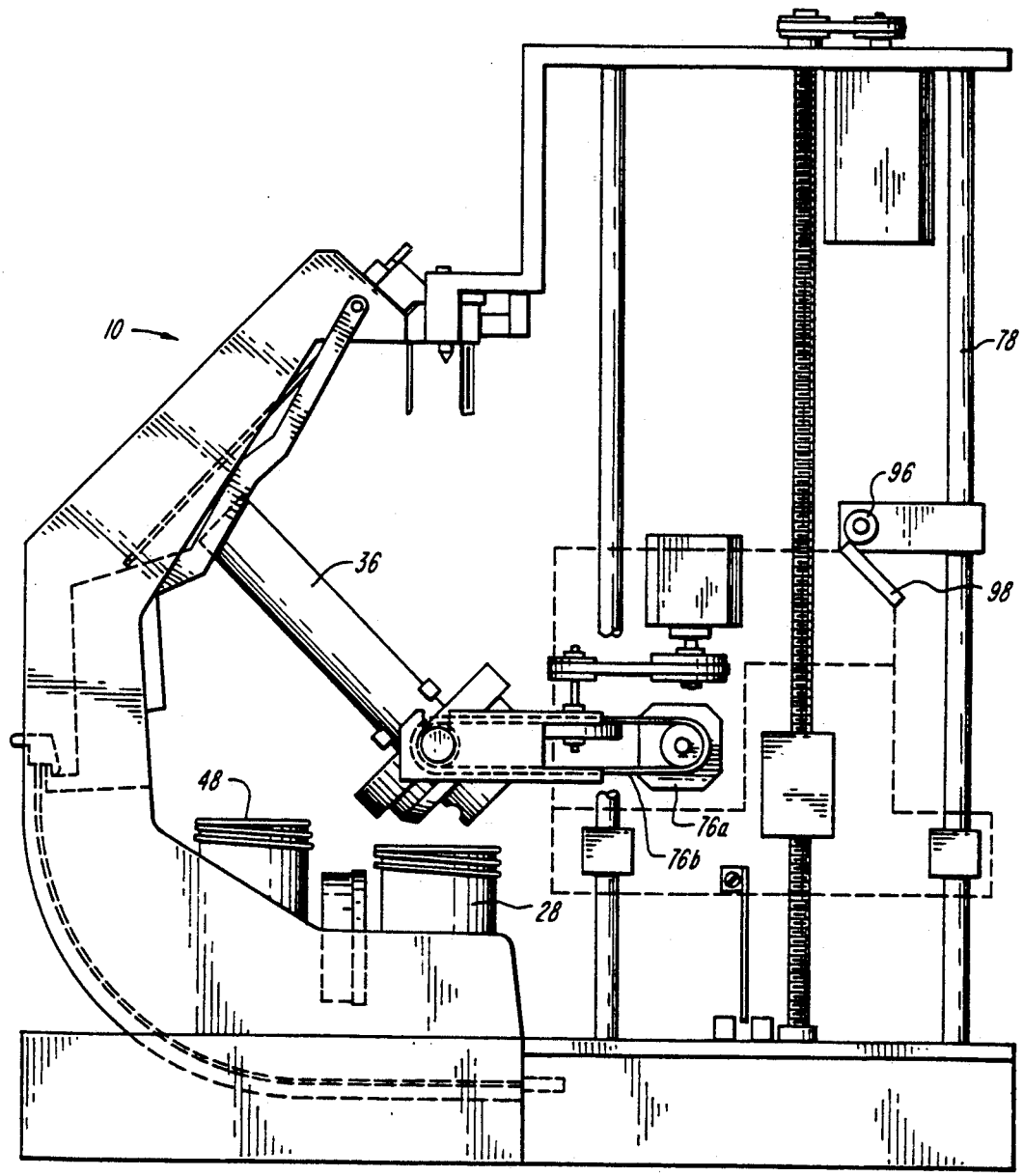

The specimen processor 64 executes a second step of this transition by actuating the tilt drive mechanism 76 to revolve the manipulator jaw mechanism 86, together with the filter device 36 clamped therein clockwise to the position shown in FIG. 8. This tilting movement is about a normally horizontal axis parallel to the horizontal axis 62 along which the cartridge reference pins 58 and 60 are aligned. A motor 76a of the tilt mechanism is coupled by a belt 76b with the jaw mechanism 76, for effecting the tilt movement.

Figure 9:
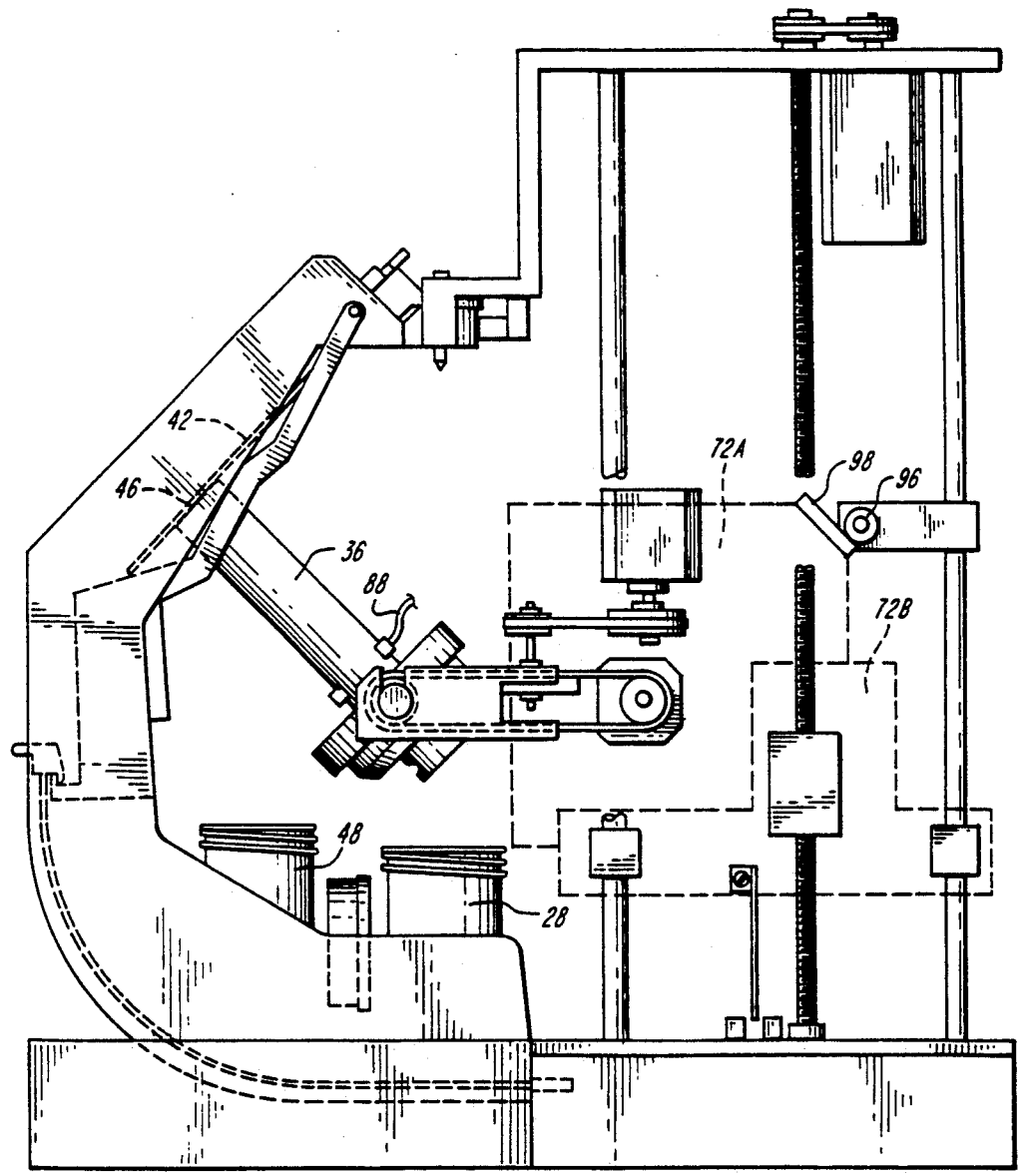

A subsequent operation of the specimen processor 64 with the illustrated cartridge 10 moves the clamped filter device 36 horizontally to the left, from the position of FIG. 8 to the extended position shown in FIG. 9. This movement abuts the screen filter 46 of the filter device against the microscope slide 42 that the cartridge carries at the support 16. This abutment of the screen filter with the microscope slide transfers cellular particles collected on the screen filter to the microscope slide. The transferred cellular particles have essentially the same spatial distribution on the microscope slide as they had on the screen filter, as is desired. A preferred concurrent operation is for the controller 71 to actuate the pneumatic system 70 to apply a small positive pneumatic pressure to the interior of the filter device 36, by way of the pneumatic clamp 90, for enhancing the lift-off of cellular particles from the screen filter and thereby enhancing the transfer of all collected cellular particles from the screen filter of the filter device to the microscope slide 42.

The illustrated specimen processor 64 affects the lateral movement of the clamped filter device 36 to the shifted or extended position shown in FIG. 9 by moving the platform 72a of the carriage 72 laterally relative to the other carriage platform 72b. The second carriage platform 72b mounts the first carriage platform 72a on two parallel and horizontally-extending slide rods 92, and a spring 94 is tensioned between the two platforms to maintain them normally in the retracted and aligned condition of FIGS. 4 through 7. Further, the processor 64 has a camming roller 96 mounted on one slide rod 78 and moveable, horizontally with a solenoid to engage selectively with an inclined ramp 98, shown in FIG. 8 on the upper right side of the platform 72a, during upward movement of the carriage 72 from the specimen collecting position of FIG. 7 to the transfer position of FIG. 9.

This engagement of the ramp on the first platform 72a with the roller 96 cams the platform 72a laterally, i.e., sideways to the left in FIG. 9, and thereby slides that platform 72a, on the slide rods 92 and against the restoring force of the spring 94, relative to the other second carriage platform 72b.

Figure 10:
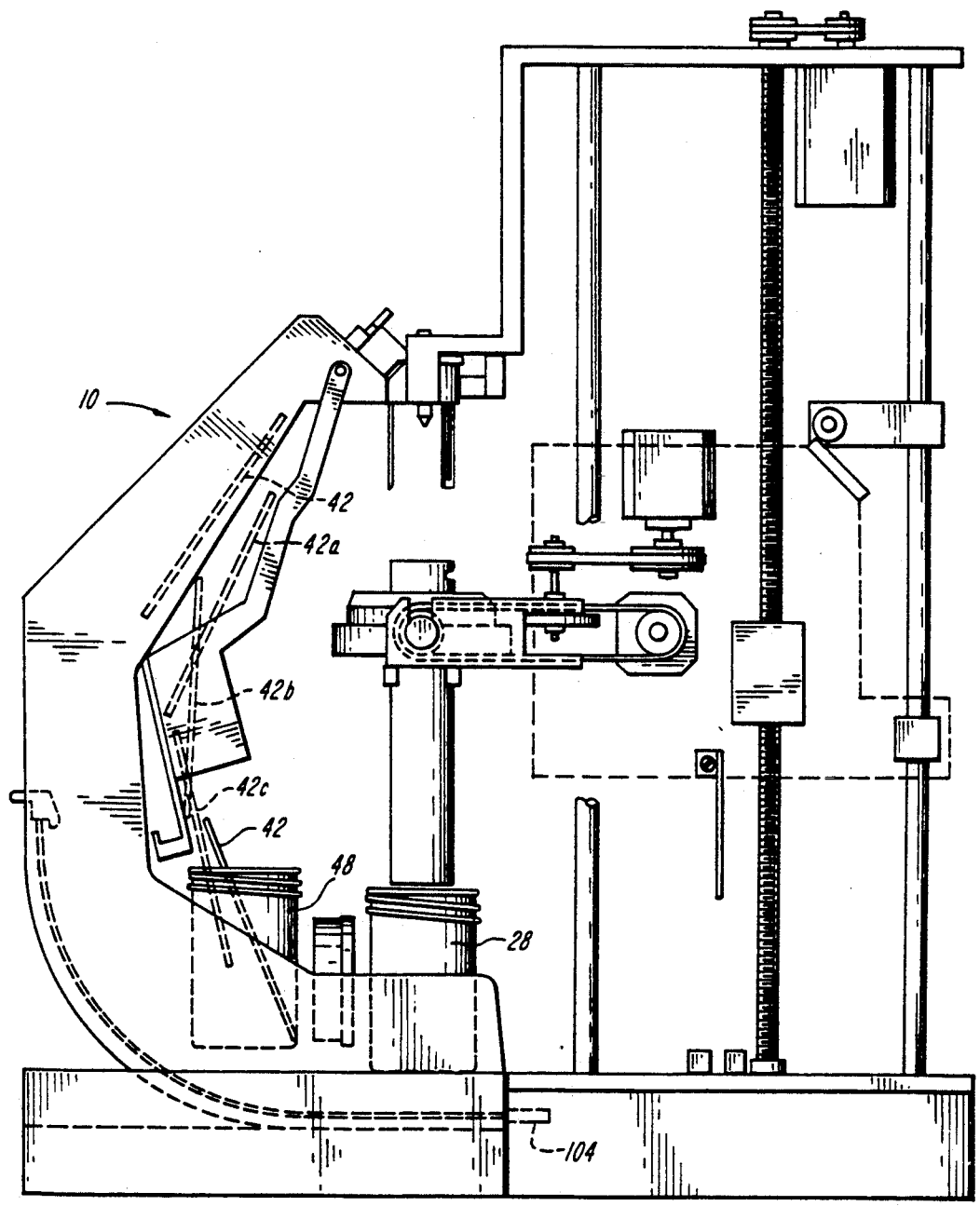

Further operation of the illustrated specimen processor 64, after completion of the specimen transfer to the microscope slide, is to retract the carriage platform 72a horizontally to the right and to return the jaw mechanism 86 of the manipulator 66 to the normal upright position. The specimen processor 64 performs these movements by lowering the carriage with the elevator motor 84 and by revolving the manipulator with the tilt motor 76a, to return the clamped filter device 36 to the upright position and centered on the vertical axis 30, as shown in FIG. 10. Thereafter, with the filter device 36 again centered on the axis 30 above the sample container 28, the specimen processor 64 can empty sample-suspending liquid, that was aspirated into the filter device 36 during the specimen collecting operation (FIG. 7), by closing the clamp 90 and applying a positive pressure to the filter device 36. This action expels the liquid through the screen filter 46 and, empties it back into the sample container 28.

Thereafter, the specimen processor 64 raises the carriage 72 and thereby raises the clamped filter device 36 to the position shown in FIG. 5. This movement returns the filter device to be seated in the socket-like receptacle 32 of the implement support 14 on the cartridge. With the clamp 90 open, to release the arms 90a and 90b from the filter device 36, the specimen processor 64 releases the jaw mechanism 86 of the manipulator 66 from clamped engagement with the filter device. The specimen processor next lowers the carriage 72 to the initial position of FIG. 4, where the manipulator 66 is entirely removed from the filter device 36.

A further operation, in the illustrated sequence, of the cartridge 10 of the invention with the specimen processor 64, is to transfer the microscope slide 42, with the cellular sample thereon, from the implement support 16 to a bath of fixative solution contained in an output container 48 seated in the output support 18. The processor 64 preferably performs this operation promptly after transferring a specimen to the slide 42 and hence prior to expelling liquid from the filter device prior to returning the filter device to the cartridge support 14. The transfer mechanism 54 of the cartridge 10 performs this slide-transferring operation, in response to the processor, by disengaging the slide from the support 16 and by guiding the released slide 42 to enter the output container 28.

More particularly, with reference to FIGURE 10, which shows elements of the cartridge 10 and the processor 64 system at the end of this operation, the illustrated processor 64 has a solenoid actuator 104 that, when actuated, depresses a spring-biased plunger 106 mounted in the cartridge base 22. As also shown, a flexible cable 108, guided in a passage 110 in the cartridge frame, couples the plunger 106 movement to a latch member 134 to operate the transfer mechanism 54.

Actuating the processor solenoid 104 to depress the plunger 106, i.e., move it leftward in FIG. 10, raises the frame-carried latch member 134 and thereby releases the cartridge transfer mechanism 54. The released mechanism moves from a retracted position shown in FIGS. 4–9, to an extended slide-transferring position, shown in FIG. 10. This transition of the transfer mechanism releases the microscope slide 42 from the cartridge support 16, and the slide gravitationally descends. The transfer mechanism guides this descent of the slide through successive positions 42a, 42b, and 42c, FIG. 10, and into the output container 48 at output support 18. Reference numeral 42d shows the final, transferred position of the slide at rest in the container 48. The commonly-assigned and concurrently filed application identified above describes the transfer mechanism 54 and this transfer operation in further detail.

After this slide transferring operation and the preferably subsequent operation of draining liquid from the filter device 36 into the sample container 28, and returning the sample container to the cartridge support 14, as discussed above, the cartridge 10 typically is removed from the engagement with the specimen processor 64, thereby readying the processor for repeating the foregoing operation with a fresh cartridge 10 carrying a fresh sample container 28 and fresh slide 42 and fresh output container 48 and fresh filter device 36.

Figure 11:
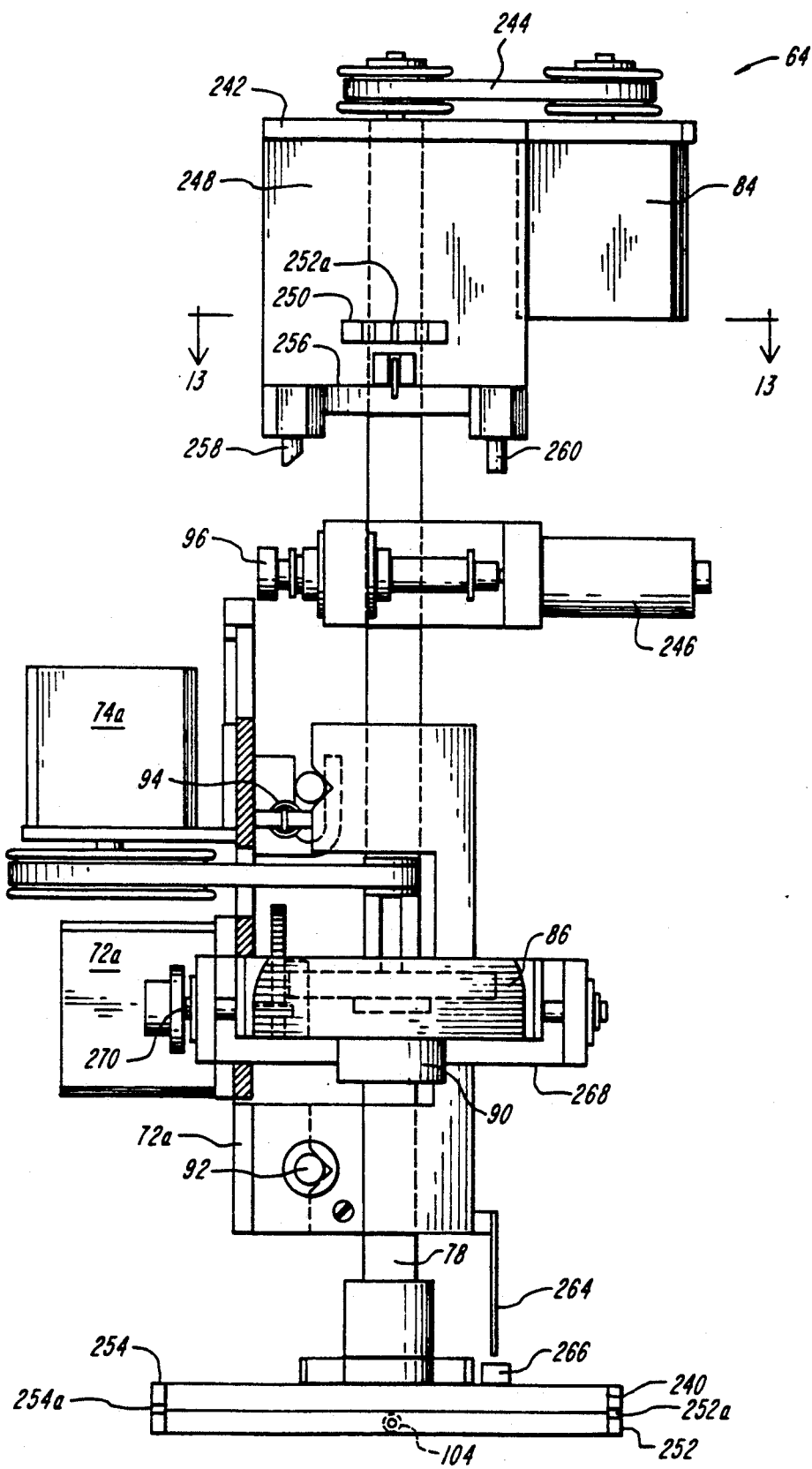
FIG. 11 is a front elevation view, simplified and fragmentary, of the specimen processor shown in FIGS. 4 through 10.
Figure 12:
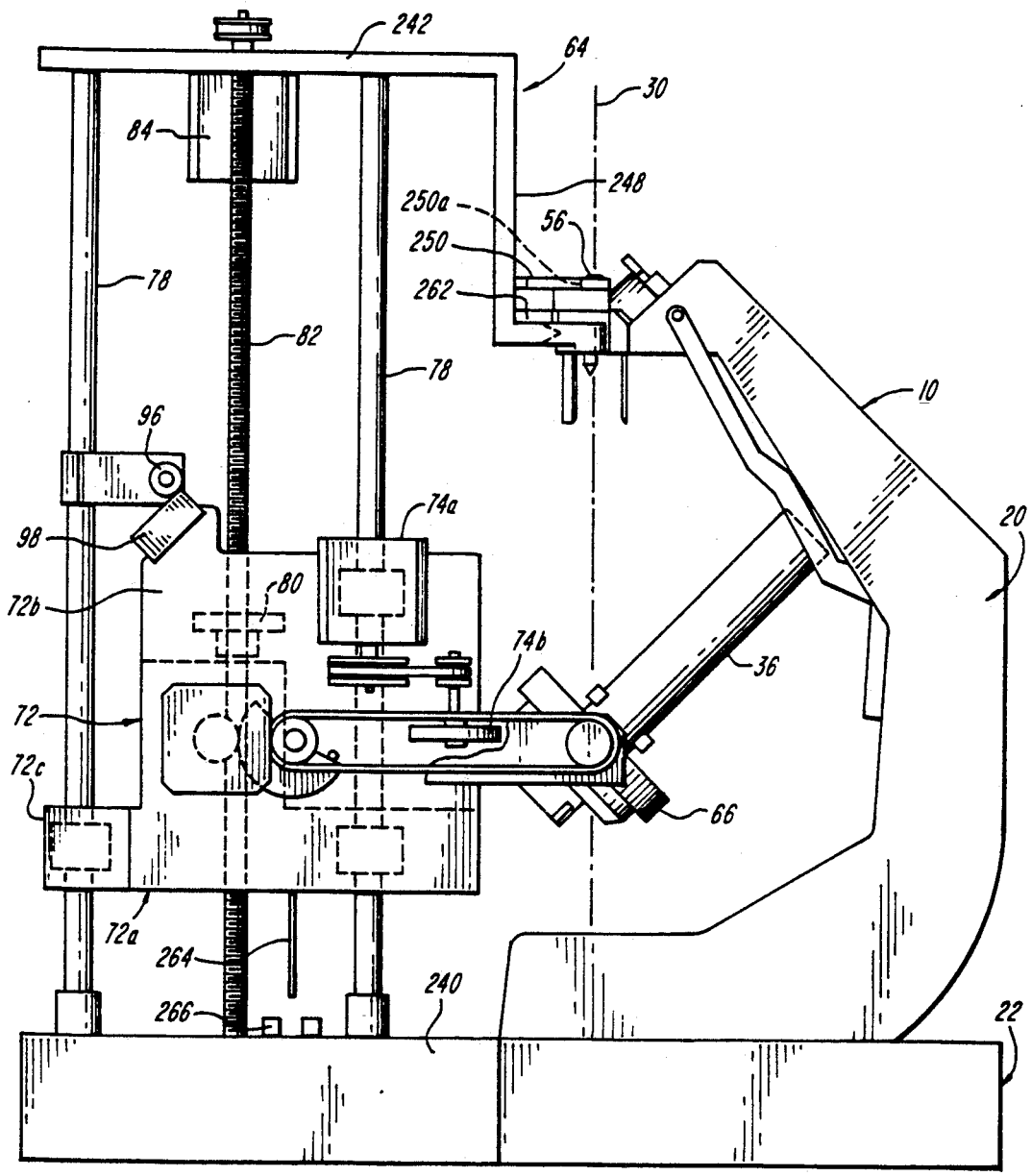
FIG. 12 is a side elevation view of the processor of FIG. 11 from the side opposite the side shown in FIGS. 4 through 10 and in the position shown in FIG. 8.

With reference to FIGS. 11, and 12, the illustrated processor 64 has a base 240 that mounts the solenoid actuator 104 and mounts the two parallel upstanding slide rods 78. An upper plate 242 is secured to the top of the slide rods, and the lead screw 88 is journaled to the base 240 and the upper plate 242 for rotation in response to the elevator motor 84, with which it is coupled by a belt 244.

The back slide rod 78, shown on the left in FIG. 12, mounts a solenoid 246 that carries the camming roll 96. The solenoid is operable, in response to the control unit 71, for selectively retracting the camming roll, as in FIG. 11 to withdraw it free of the travel of the carriage 72, and, alternatively, to extend the camming roll to engage the ramp 98 on the carriage 72, as in FIGS. 8, 9 and 12.

Figure 13:
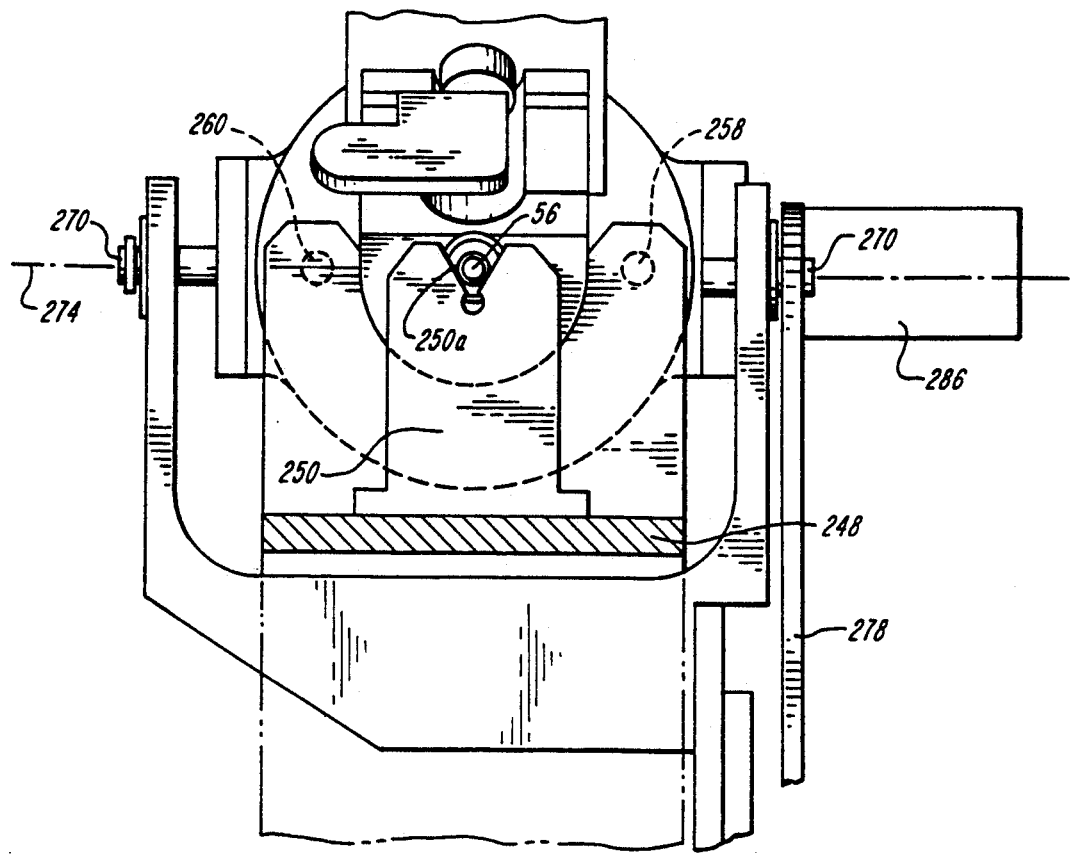
FIG. 13 is a top plan view of the processor according to the invention taken along line 13—13 of FIG. 11.

As further shown in FIGS. 11 and 12, the upper plate 242 mounts a bracket 248 that extends to the front of the processor, i.e. to the right in FIG. 12. A normally horizontal reference arm 250 extends forward from the bracket 248 and is recessed at the front end with a funnel-like tapered aligning notch 250a. The aligning notch 250a, as shown in FIG. 13, receives the cartridge pin 56 for, together with the cartridge pins 58 and 60, aligningly engaging the cartridge 10 with the processor 64.

The processor base 240 carries two further reference arms 252 and 254, normally extending horizontally and to the front from the base on either side and each similarly recessed with a funnel-like, tapered aligning notch 252a and 254a. The notches 252a and 254a aligningly receive and seat the cartridge pins 58 and 60, respectively, when the cartridge 10 is in operative aligned engagement with the processor. In the illustrated processor 64, the three aligning notches 250a, 252a, and 254a are located at the corners of a triangle that lies in a vertical plane that coincides with the axis 30, FIG. 4, when the processor is engaged with a cartridge 64.

The processor front bracket 248 carries a further normally horizontal arm 256, below the reference arm 250 and from which depend two pins 258 and 260, preferably aligned, coplanar, and parallel with the cartridge pin 56 when the processor is engaged with a processor 10. The pins 258 and 260 preferably lie in the same plane, parallel to the plane of FIG. 11, as the three aligning notches 250a, 252a, and 254a.

A further element on the processor bracket 248 is a sensor 262 that disposes a sensor finger 262a to sense when a cartridge 10 engaged with a processor has a filter device 36 seated in the cartridge support 14. In particular, the illustrated sensor finger 262a projects into the sensor aperture 148 in the front of the cartridge support 14 as FIG. 1 shows. The sensor 262 includes a microswitch connected with the processor control unit 70.

Figure 15A:
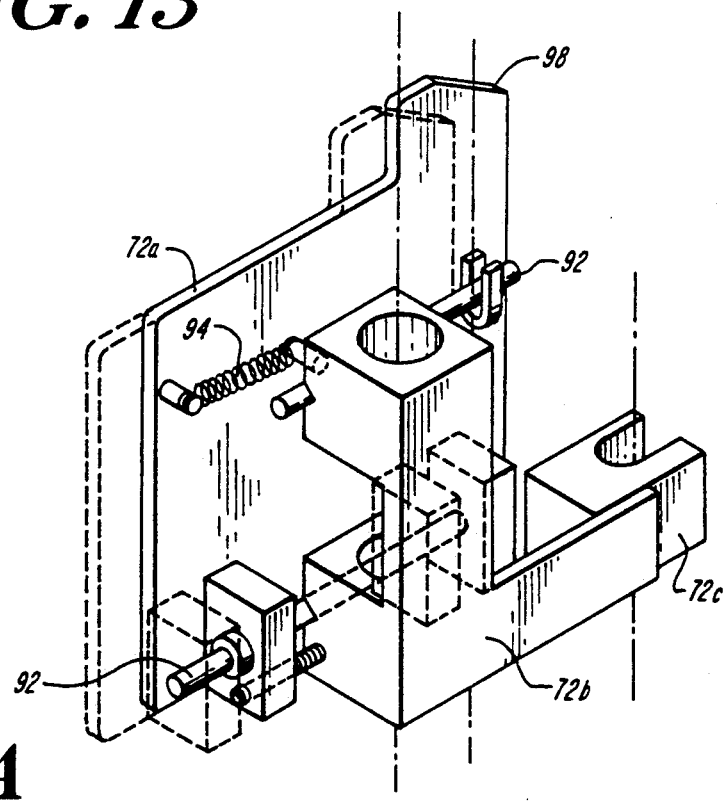
FIG. 15A is a fragmenting perspective view showing the carriage of the processor of FIG. 11.

With reference to FIGS. 11 and 12 and the simplified fragmentary view of FIG. 15a, the platform 72b of the cartridge 72 is journaled to slide on the front rod 78 and carries a bifurcated guide 72c that slideably engages the back rod 78. The nut block 80, which threadably engages the lead screw 82, is secured to the carriage platform 72b by way of a flexure mounting. This flexure mounting and the bifurcated guide 72c allow the platform 72b to slide vertically on the front slide rod 78, in response to rotation of the lead screw, and to remain fixed in a single vertical plane, without binding. The platform 72b mounts two horizontally extending and parallel slide rods 92 on which the carriage platform 72a slideably mounts. The spring 94 is tensioned between the two platforms 72a and 72b to resiliently bias the carriage platform 72a to the back of the processor, i.e., to the position shown in FIGS. 4 through 8 and in solid lines in FIG. 15a. As described above, the carriage platform 72a carries the camming ramp 98 that selectively engages the camming roll 96 for deflecting and thereby shifting the platform 72a forward on the processor, to the position shown in FIG. 9 and in phantom in FIG. 15a with a sliding movement along the upper and lower slide rods 92. This forward movement of the platform 72a further tensions the spring 94, which returns the platform 72a to its normal, backmost position when the ramp 98 is free of the camming roll 96.

As also shown in FIGS. 11 and 12, the carriage platform 72b carries a sensor flag 264 that triggers a position sensor 266 illustratively mounted on the processor base 240, for signalling the controller 71 when the carriage 72 is in the lowermost position.

The specimen processor 64 preferably has a counterweight (not shown) coupled by way of a conventional cable and pulley linkage with the carriage platform 72b. The counerweight moves vertically opposite to the elevational movement of the carriage 72, and thereby offsets momentum of the transport movement and facilitates control of the transport movement and positioning.

The illustrated manipulator 66 of the processor 64 mounts the circular jaw mechanism 86 on a yoke 268, the base of which is secured to the carriage platform 72a, FIGS. 11 and 13. A pair of axle pins 270, 270 project from a tilt plate 272 of the manipulator jaw mechanism along a normally horizontal axis 274 that is parallel to the cartridge axis 62 when the processor is aligningly engaged with a cartridge and that is parallel to the axis along which the aligning notches 252a and 254a are arranged. The axle pins 270 are journaled to yoke arms 268a at the front of the processor 64 to locate the axis 274 to intersect the axis 30 (FIG. 12) when the processor is aligned and engaged with a cartridge 10.

One axle pin 270 is keyed to a pulley engaged with a belt 278 for tilting the circular jaw mechanism about the axis 274, as shown for example in FIG. 8, and as described further below.

The tilt plate 272 mounts the caliper-like clamp 90 having clamp arms 92a and 92b, and mounts the solenoid 286 that operates the clamp.

When the clamp 90 is closed, the arms 90a and 90b clamp against a filter device 36 (FIG. 3) to couple the pneumatic hose 88 secured to the clamp arm 90a to the filter device passage 42b as shown, for example, in FIG. 7. Alternatively, when the clamp 90 is open, the clamp arms are spread further apart and spaced radially outwardly from the filter device, as appears, for example, in FIG. 6.

Figure 15:
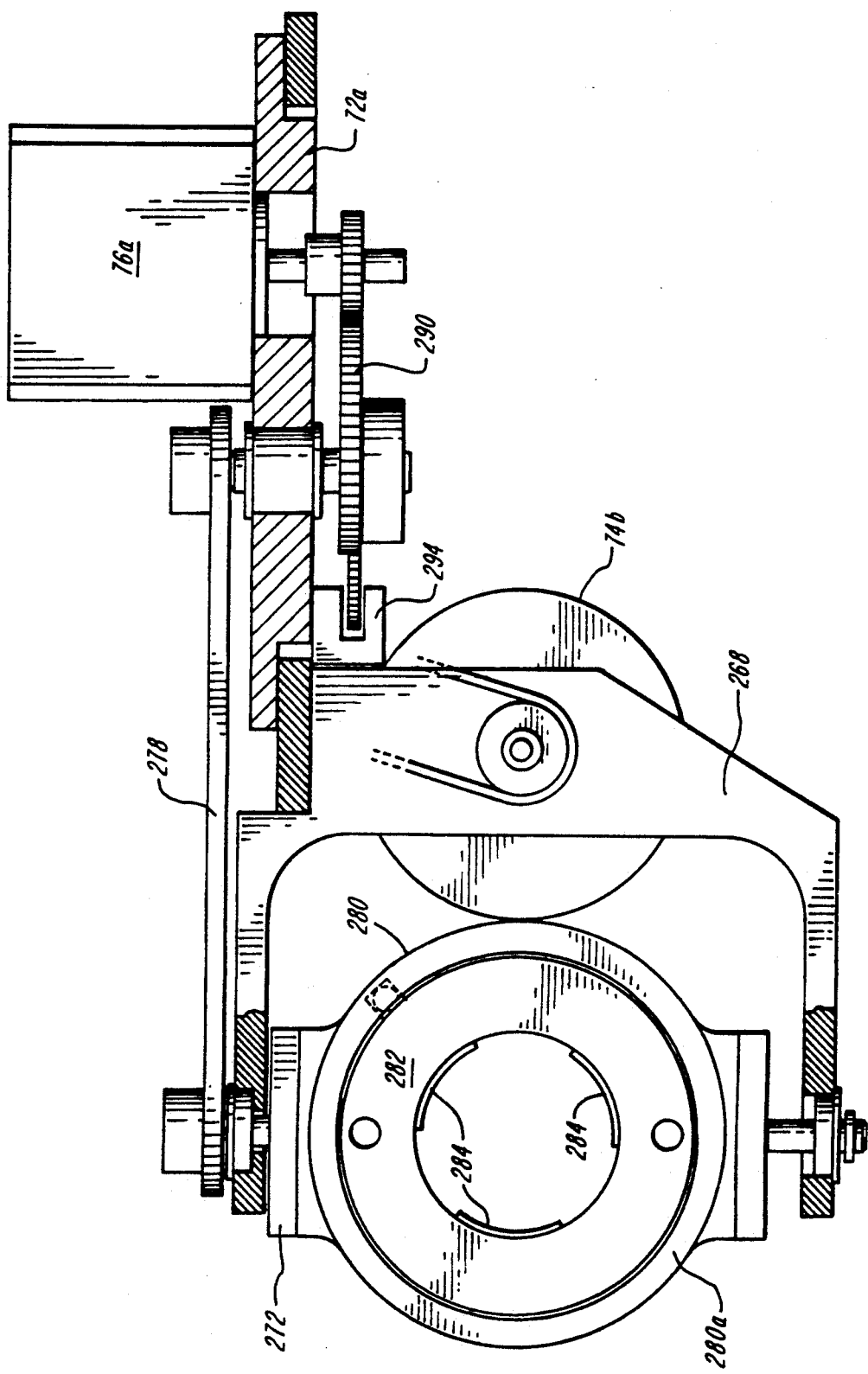
FIG. 15 is a top plan view of the preferred tilt drive mechanism of FIG. 9.
Figure 16:
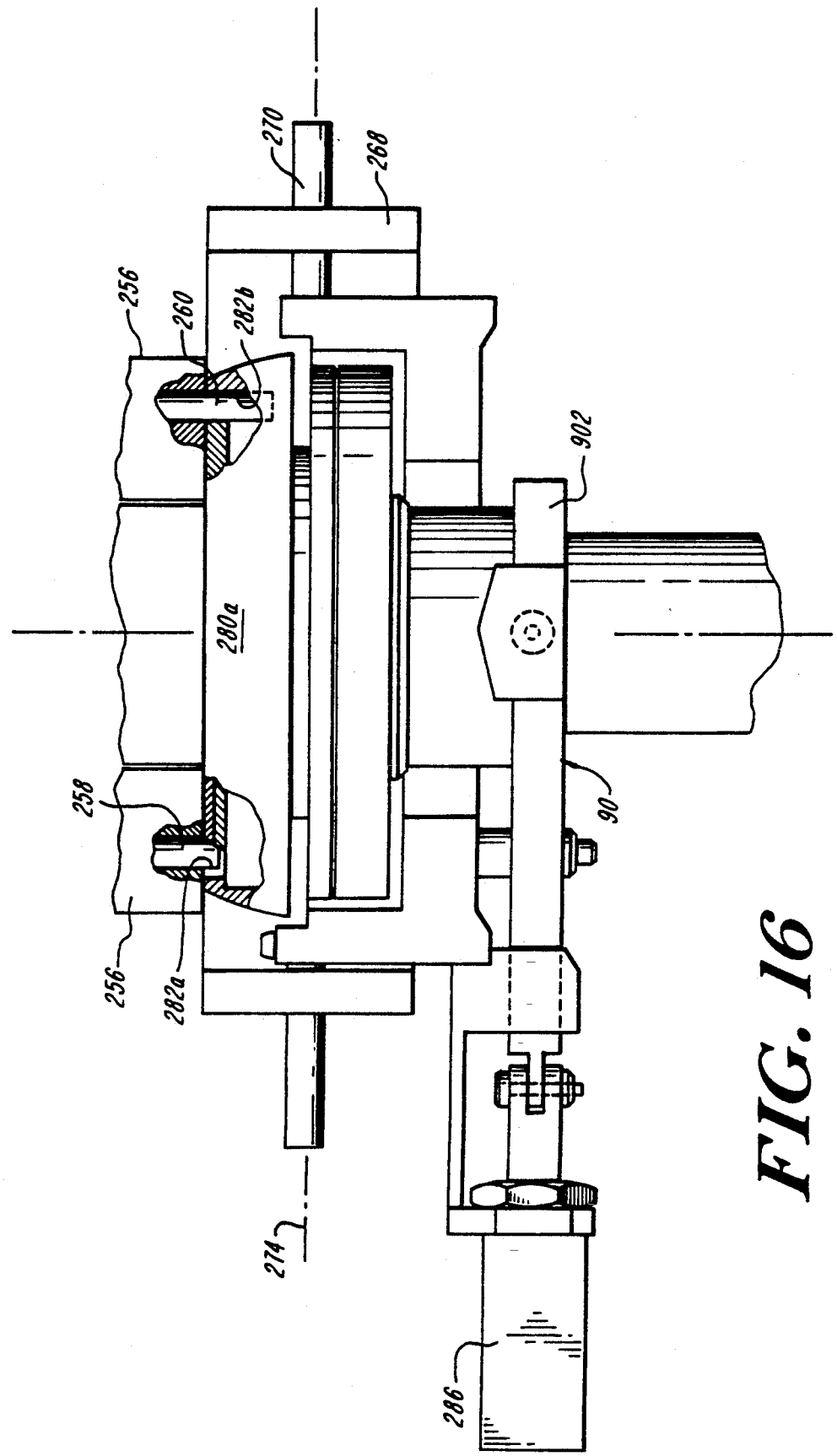
FIG. 16 is a fragmenting side elevation view, partly in section, of a jaw mechanism for the processor of FIGS. 11 and 12.

With reference to FIG. 16, a circular drive ring 280 is mounted by bearings on the tilt plate 272 for rotation, e.g. about the axis 30, relative to the plate. The drive ring 280 has an outer rim 280a that the drive wheel 74b engages for rotating the manipulator 66. A circular clamp ring 282 is mounted on the drive ring 280, at the top and concentrically within the rim 280a. The clamp ring 282 forms part of a detent mechanism that normally locks the clamp ring to rotate with the drive ring 280. The detent mechanism can be shifted from this normal condition to a release condition, where the drive ring 280 can rotate relative to the clamp ring 282. This differential or relative rotation cams clamp pads 284, shown in FIG. 15, of the jaw mechanism 86 into or out of clamping engagement with a filter device 36.

As shown in FIGS. 13 and 16, the clamp ring 282 has two diametrically located holes 282a and 282b that seatingly receive the bracket mounted pins 258 and 260, when the manipulator 86 is raised to the uppermost clamping position of FIG. 5. When seated in the clamp ring hole 282a, the pin 258 releases the detent mechanism to allow the drive ring 280 to rotate relative to the clamp ring. The other pin 260, when seated in the clamp ring hole 282b, holds that clamp ring stationary, i.e., prevents rotation even when the drive ring 280 is rotated. The three clamp pads 284 of the circular jaw mechanism 86 are cammed to move radially in response to rotation of the drive ring 280 relative to the clamp ring 282.

As FIGS. 11 and 15 show, the motor 74a is coupled with the circular jaw mechanism 86 for rotating the drive ring 280, to provide the clamping and release operation of the manipulator 66 and to provide the dispersing operation described with reference to FIG. 6. The rim drive wheel 74b that drives the manipulator via the drive ring rim 280a, is journal mounted to the yoke 268 is driven by the motor 74a through a belt and pulley mechanism.

The jaw mechanism 86 has a position sensor, connected with the system control unit 71, FIG. 4, and preferably employing a magnetic sensor on the tilt plate 272 and a sensor magnet on the drive ring 280. Rotational alignment of the ring-carried magnet with the non-rotating sensor designates a "home" position, that enables the control unit 71 to operate the motor 74a to attain any desired orientation of the jaw mechanism about the axis 30. To facilitate this control, the motor 74a is preferably a stepping motor, as are each of the other motors 84 and 76a.

The spin drive mechanism 74 of the processor 66 preferably provides an adjustable engagement of the rim drive wheel 74b with the rim 280a of the drive ring 280. An adjustably positioned mount (not shown) of the rim drive wheel 74b to the yoke 268, FIG. 15, is selectively movable to change the rim drive engagement between a relatively low contact pressure and a relatively high contact pressure. The former may be desired for spinning the filter cylinder for the disperse operation, FIG. 6, and during tilting of the manipulator into and out of the horizontal position of FIG. 11. The latter, high pressure engagement, may be desired for clamping and unclamping a filter cylinder.

Figure 14:
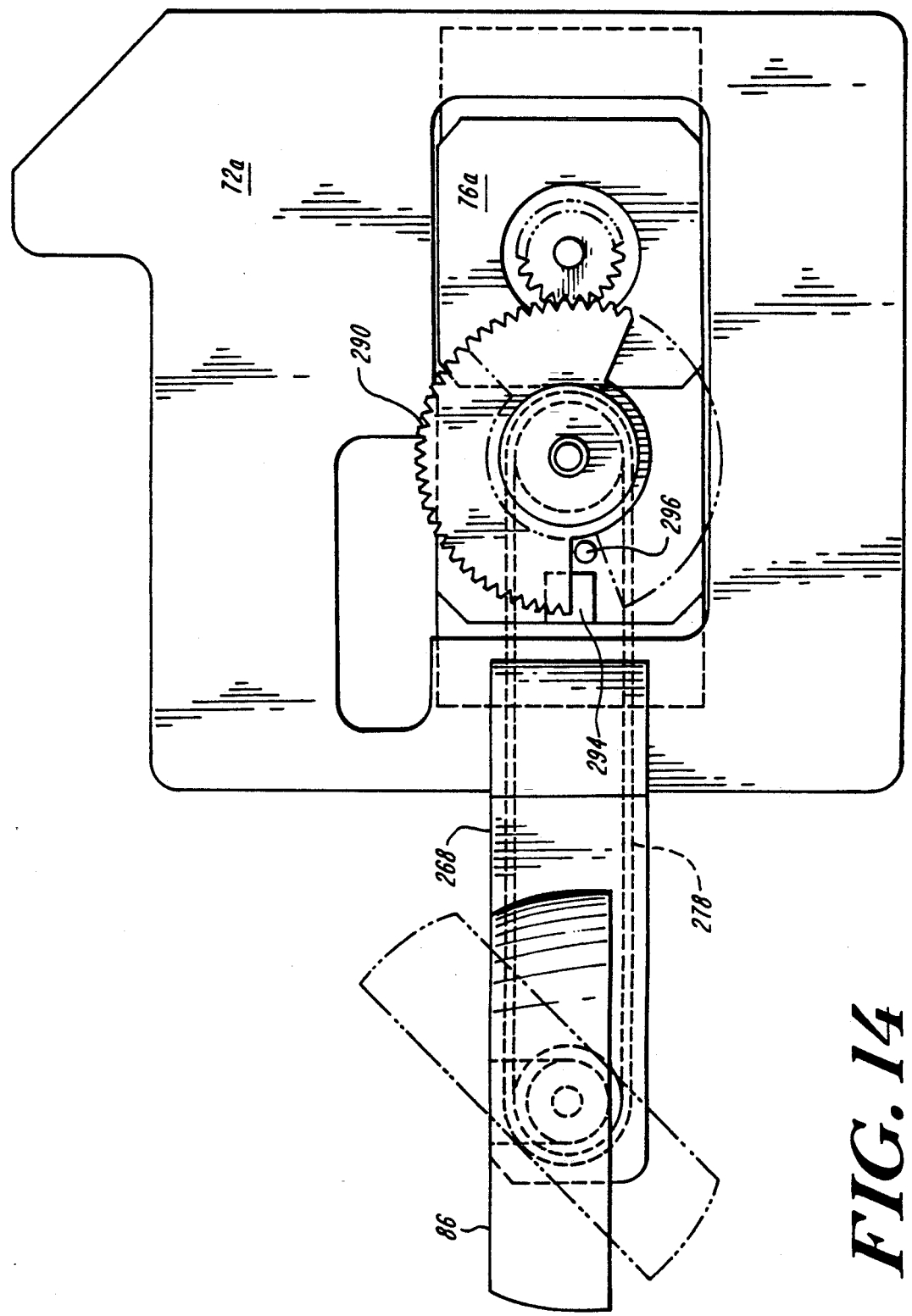
FIG. 14 is a fragmentary side elevation view of a preferred construction of the processor tilt drive mechanism.

The tilt drive mechanism 76 of the processor 64, illustrated schematically in FIGS. 4 through 10, preferably employs a sector gear arrangement as FIGS. 14 and 15 show. In particular, in the illustrated arrangement, the tilt drive motor 76a is mounted on the platform 72a, as is the spin drive motor 74a (FIG. 11), and is coupled to a sector gear 290. A pulley is coupled to rotate with the sector gear and the belt 278 couples the rotation to the tilt plate 272 of the actuator jaw mechanism. Accordingly, rotation of the sector gear 290 by the motor 76a is coupled by the belt 278 to tilt the jaw mechanism between the normally horizontal position of FIG. 11 through an arc of approximately 135° to the specimen transferring position shown in FIG. 12. FIG. 14 shows the former position in solid lines and the latter position with broken lines, i.e., in phantom.

FIGS. 14 and 15 further show that an optical sensor 294 senses when the sector gear attains the horizontal position. Further, a stop pin 296 is provided to engage either radial edge of the sector gear 290 in the event of a malfunction that would otherwise tilt the manipulator beyond the extremes of the desired orientations.

With further regard to the operation of the illustrated processor 64, when the manipulator 66 is in the raised position of FIG. 5 to clamp a filter device 36 carried on a cartridge 10 engaged with the processor 64, the illustrated vertically extending pins 258 and 260 carried on the bracket 248 seat in the holes 282A and 282B, respectively, of the clamp ring 282. One pin releases the detent mechanism that locks the clamp ring and drive ring to rotate together. The other pin holds the clamp ring 282 so that it cannot rotate, i.e. about the axis 30.

Subsequent rotation of the drive ring 280, by way of the rim-driving wheel 74b driven by the motor 74a, accordingly produces differential rotation between the two ring elements 280 and 282 that cams the jaw clamp pads 284 radially inward into clamping engagement with a filter device 36. The rotation inhibiting pin 280 is longer than the detent-operating pin 258, so that upon initial downward movement of the manipulator 66, the longer pin 280 prevents differential rotation, thereby holding the pads 284 clamped against the filter device 36, until the detent mechanism is again locked. Continued downward movement of the manipulator accordingly carries the filter device with the manipulator for subsequent operations as described.

During the subsequent operation illustrated in FIG. 6, for dispersing sample material in the container 28 by rotating the clamped filter device 36 about the axis 30, the two manipulator ring elements 280 and 282 are locked for co-rotation in response to drive from the motor 74a as applied by the rim-driving wheel 74b.

Subsequently, at the end of the illustrated operating cycle described above, when the specimen processor 64 has completed the operations discussed above with reference to FIGS. 5-10, and again raises the manipulator 66 toward the position shown in FIG. 5 for returning the filter device 36 to the cartridge 10, the processor can rotate the two ring elements 280 and 282 together, by way of the motor 74a and rim-driving wheel 74b, to align the filter device 36 tab 44a (FIG. 3) with the key-like axial slot 34 of the cartridge support 14 (FIG. 1). Upon raising the manipulator 66 further, the two bracket-carried pins 258 and 260 again enter the holes in the clamp plate 282. This action again allows the two ring elements to rotate with respect to each other and holds the clamp ring stationary. Subsequent rotation of the drive ring 280, opposite to the rotation for clamping action, releases the jaw clamp pads 284 from the filter device 36. The specimen processor 64 can then lower the manipulator 66, leaving the filter device 36 seated in the cartridge support 14, back to the initial position shown in FIG. 4.

With further reference to the pneumatic coupling clamp 90, in addition to being closed to clamp the arms 90a and 90b against the filter device 36 for coupling the pneumatic system 71 with the passage 44b, during the specimen collecting operation of FIG. 7, the clamp 90 is preferably maintained closed during the subsequent operations of FIGS. 8 and 9. Further, the pneumatic control systems 71 preferably maintains a relatively negative pressure within the chamber of the filter device, to maintain a pressure differential across the screen filter 46 of the filter device for holding collected cellular particles onto the screen filter, as the processor 64 first raises the filter device 36 upward out of the sample container 28 and as it tilts the filter device to the inclined position of FIG. 8, and further as it moves the filter device to abut the screen filter 46 with a microscope slide 42 carried on the cartridge support 16, FIG. 9. As noted above, at this juncture the pneumatic system 71, typically together with the controller 70, changes the pressure signal applied to the filter device passage 42b and establishes a slight positive pressure in the chamber of the filter device, thereby to, in effect, blow or lift collected cellular particles from the screen filter 46 to facilitate the transfer of all collected cellular particles to the microscope slide 42.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention described herein, and all statements of the scope of the invention which as a matter of language, might be said to fall therebetween.

Having described the invention, what is claimed as new and secured by Letters Patent is:

We claim:

1. Apparatus for processing multiple particle-suspending liquid samples in succession without contamination between different samples, said apparatus processing each sample with a filtration separation device having a filter element and a chamber, said apparatus comprising A. frame means having reference surface means for removably and replaceably aligningly engaging holder apparatus that removably and replaceably supports the filtration separation device and that supports a container of a particle-suspending liquid sample, B. motive means carried on said frame means (i) for removing the separation device from support by holder apparatus with which said reference surface means is aligningly engaged, and (ii) for introducing the filter element of that device into the particle-suspending liquid sample, for the collection of particles from the liquid onto the filter element, and (iii) for returning the separation device to support by holder apparatus with which said reference surface means is aligningly engaged.

2. Apparatus according to claim 1 wherein said motive means includes means for removably and replaceably disposing the filter element of the separation device, when removed from support by holder apparatus, into a substantially face-to-face relationship with a spatial plane at which holder apparatus mounts a viewing slide, for the transfer of particles from the filter device to the viewing slide.

3. Apparatus as set forth in claim 1 wherein said motive means includes means for introducing the separation device into the particle-suspending liquid sample and for moving the device relative to the liquid for creating shear forces in the particle-suspending liquid sample prior to the collection of particles from the liquid onto the filter element.

4. Apparatus according to claim 1 wherein said motive means includes manipulation means for selectively and releasably clampingly engaging the separation device and removing it from support by the holder apparatus.

5. Apparatus according to claim 4 further comprising coupling means for selectively and releasably coupling the separation device engaged with the manipulation means to a pressure source for inducing a flow of the particle-suspending liquid sample across the filter element.

6. Apparatus according to claim 5 wherein said coupling means is carried by said manipulation means.

7. Apparatus for processing multiple particle-suspending liquid samples in succession without contamination between different samples, said apparatus processing each sample with a separation device having a filter element, and comprising A. frame means having reference surface means for removably and replaceably aligningly engaging holding apparatus that removably and replaceably supports the separation device and that supports a container of a particle-suspending liquid sample, B. means for removing the separation device from support by holder apparatus engaged with said frame means, and C. means for removably and replaceably disposing the filter element of the separation device, when removed from support by the holder apparatus, into substantially face-to-face relationship with a spatial plane at which the holder apparatus mounts a viewing slide, for the transfer of particles from the filter element to the viewing slide.

8. Apparatus according to claim 7 further comprising said coupling means for selectively and releasably coupling the separation device to a pressure control source for subjecting the filter element to a pressure differential that facilitates said transfer of particles.

9. Apparatus according to claim 7 for operation with holder apparatus has transfer means for moving the viewing slide from the spatial plane to an output container carried on the holder apparatus and further comprising means mounted with said frame means for selectively actuating the transfer means on holder apparatus engaged with said frame means.

10. A method for processing multiple particle-suspending liquid samples in succession without contamination between different samples, said method comprising the steps of A. mounting on holder apparatus, relative to a reference means thereon, a fluid-confining vessel having a filter element and a container of particle-suspending liquid, B. engaging the reference means of the holder apparatus with reference means on specimen preparation apparatus to align the fluid-confining vessel and the container for interaction with the preparation apparatus, C. operating the preparation apparatus to remove the fluid-confining vessel from support by the holder apparatus and to introduce the filter element thereof into the particle-suspending liquid sample, for the collection of particles from the liquid onto the filter element, and D. operating the preparation apparatus to return the fluid-confining vessel to support by the holder apparatus aligningly engaged therewith.

11. A method according to claim 10 further comprising the step of disposing the filter element of the fluid-confining vessel, after the collection of particles on the filter element, into a substantially face-to-face relationship with a spatial plane at which the holder apparatus supports a viewing slide, for the transfer of collected particles from the filter element to the viewing slide.

12. Apparatus for the preparation, from a biological sample, of a clinical specimen of cellular particles for optical examination, said apparatus comprising A. frame means for removable and replaceable alignment and operative engagement with holder apparatus carrying a biological sample and carrying a filter device, and having reference surface means for removable and replaceable positional alignment with the holder apparatus, and B. motive means on the frame means for removably and replaceably engaging the filter device on holder apparatus operatively aligned and engaged with said frame means, C. said motive means being adapted
    (i) for collecting, on the filter device engaged therewith, cellular particles from a biological sample carried on the engaged holder apparatus and wherein the collected cellular particles have a distribution for optical examination,
    (ii) for returning the engaged filter device to carrying by the engaged holder apparatus, and
    (iii) for release from the engaged filter device carried on the engaged holder apparatus, whereby, upon completion of said preparation of a clinical specimen, all implements that contact the sample are on the holder apparatus, including the collected cellular particles with the distribution for optical examination.

13. Apparatus according to claim 12 for operation with holder apparatus that carries a specimen viewing screen and wherein said motive means includes
- transport means for operation with the engaged filter device for the transfer of collected cellular particles on the filter device to a viewing screen carried on the engaged holder apparatus.

14. Apparatus according to claim 12 for operation with holder apparatus that carries a specimen viewing screen and in which said motive means includes means for transporting the engaged filter device into selected abutment with the viewing screen carried on the engaged holder apparatus, prior to said return of the filter device to carrying by the engaged holder apparatus and prior to said release from the filter device.

15. Apparatus according to claim 12 in which said motive means includes manipulation means for holdingly engaging the filter device and for replaceably removing an engaged filter device with respect to carrying by holder apparatus operatively aligned and engaged with said frame means, and for translating the engaged filter device in at least two directions and for rotating it about at least one axis.

16. Apparatus according to claim 12 for operation with a filter device that includes a chamber and further comprising
- means mounted with said frame means for replaceably and removably coupling a selected pressure signal to the chamber of the filter device engaged with said motive means for selectively drawing liquid into the filter device chamber and for sensing pressure in the filter device chamber.

* * * * *